United States Patent [19]

Hsu

[11] Patent Number: 5,354,862

[45] Date of Patent: Oct. 11, 1994

[54] PREPARATION AND THE USE OF HALOPROPARGYLATED CYCLIC QUATERNARY AMMONIUM COMPOUNDS AS ANTIMICROBIAL AGENTS

[75] Inventor: Adam C. Hsu, Lansdale, Pa.

[73] Assignee: Rohm and Haas Company, Philadelphia, Pa.

[21] Appl. No.: 114,721

[22] Filed: Aug. 31, 1993

Related U.S. Application Data

[60] Division of Ser. No. 948,367, Sep. 21, 1992, Pat. No. 5,266,567, which is a continuation-in-part of Ser. No. 782,358, Oct. 24, 1991, abandoned.

[51] Int. Cl.$^5$ ............... C07D 295/067; C07D 211/20
[52] U.S. Cl. ........................... 544/171; 540/531; 544/581; 546/248; 548/146; 548/341.5; 548/562
[58] Field of Search ............... 544/171, 58.1; 540/531, 540/248; 548/146, 341.5, 562

[56] References Cited

U.S. PATENT DOCUMENTS

| | | | |
|---|---|---|---|
| 2,971,006 | 2/1961 | Mayhew et al. | 260/309 |
| 3,506,666 | 4/1970 | Morris | 260/268 |
| 4,202,894 | 5/1980 | Pfiffner | 544/173 |
| 4,233,055 | 11/1980 | Martin | 71/76 |
| 4,301,284 | 11/1981 | Buschman et al. | 544/106 |
| 4,400,380 | 8/1983 | Ritter et al. | 564/288 |
| 4,472,412 | 9/1984 | Buschman et al. | 548/578 |
| 4,521,412 | 6/1985 | Schmitt et al. | 564/288 |

OTHER PUBLICATIONS

J. Org. Chem., 24, 1607 (1959).
J. Pharmacol. Exptl. Therap. 121, p. 347 (1957).
Kai et al. Chem. Abstracts, vol. 70 (1969), No. 11109p (Abstract of Japan 67-26,603, Dec. 16, 1976).

*Primary Examiner*—Robert Gerstl
*Attorney, Agent, or Firm*—Michael B. Fein

[57] ABSTRACT

Antimicrobial compounds of the formula

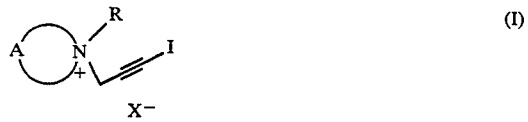

(I)

wherein
R is selected from (A)($C_1$ to $C_{20}$) straight or branched alkyl, optionally substituted with hydroxy, halogen, alkoxy, phenoxy, or —C(=O)R' wherein R' is selected from $C_1$-$C_{20}$)alkyl, ($C_1$-$C_{20}$)alkoxy, phenoxy, or NHR" wherein R" is ($C_1$-$C_6$)alkyl or phenyl; (B) benzyl; (C) phenethyl; (D) cyanoethyl; (E) 2-cyanoethyl; (F) propargyl; and (G) allyl;
X=halogen (chlorine, bromine, or iodine), phosphate, acetate, benzoate, citrate, tartrate, alkyl- or aryl-sulfonate, alkylsulfate; and

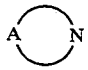

represents a 3-to 7-membered ring that contains at least one nitrogen atom optionally substituted with one or more substituents selected from ($C_1$-$C_3$)alkyl, halo, and carboxyl, said ring optionally containing one or two hetreoatoms in addition to said one nitrogen atom, selected from sulfur, oxygen, and a second nitrogen;

Processes for inhibiting microbial growth, and compositions suitable therefore are also disclosed.

2 Claims, No Drawings

PREPARATION AND THE USE OF HALOPROPARGYLATED CYCLIC QUATERNARY AMMONIUM COMPOUNDS AS ANTIMICROBIAL AGENTS

This is a divisional of U.S. patent application Ser. No. 07/948,367, filed Sep. 21, 1992, now U.S. Pat. No. 5,266,567 which is a continuation-in-part of U.S. patent application Ser. No. 07/782,358, filed Oct. 24, 1991, now abandoned.

I. BACKGROUND OF THE INVENTION

A. Field of the Invention

This invention relates to novel quaternary ammonium antimicrobial compounds and their use.

B. Description of the Prior Art Quaternary ammonium compounds having the general formula (A):

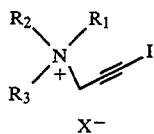

(A)

wherein $R_1$, $R_2$, and $R_3$ are all substituted or unsubstituted carbon chains were disclosed in U.S. Pat. No. 4,521,412 as having antifungal and antibacterial activity.

Tropium quaternary ammonium compounds having the general structure (B):

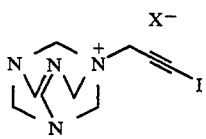

wherein X=chlorine were evaluated for hypotensive activity in J. Org. Chem., 24, 1607 (1959). No antimicrobial activity was mentioned in this paper.

The chloride salt and saccharinate salt of tropium (C) (i.e. X=saccharine) were mentioned in U.S. Pat. No. 4,521,412.

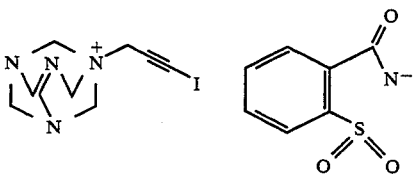

(C)

Cyclic quaternary ammonium compounds which do not contain an iodopropargyl group have been disclosed in J. Pharmacol. Exptl. Therap., 121, p.347 (1957), where piperazine mono-quaternary salts were shown to have activity against mouse pinworm.

U.S. Pat. No. 4,233,055 discloses substances of the following general structure (D) for inhibiting the growth of plants and for promoting the ripening and abscission of fruit.

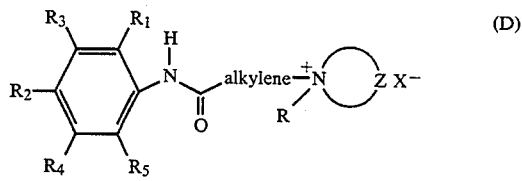

(D)

R=alkyl, alkenyl, alkynyl

Cyclic quaternary ammonium compounds have been claimed to be used as surface active agents, bactericides, biocides, algicides or fungicides, as exemplified by the following:

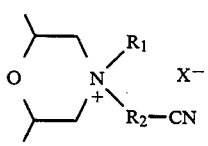

DD-278-268-A, Fungicides

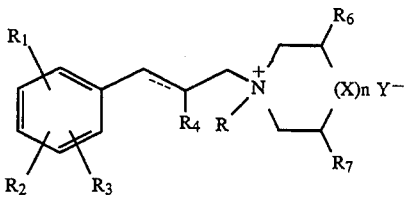

U.S. Pat. No. 4,472,412 (1984), Fungicides

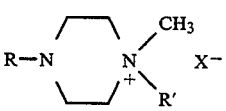

U.S. Pat. No. 3,506,666 (1970), For the control of algae, bacteria and fungi.

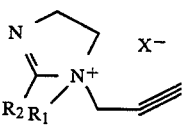

U.S. Pat. No. 2,971,006 (1961), claimed to be used as surface active agents, bactericides, biocides, and particularly as fungicities.

Japanese Patent 67-026603B discloses a method of producing 3-halo-2-propynylamines of the formula

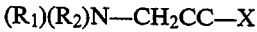

$(R_1)(R_2)N-CH_2CC-X$ in which $R_1$ and $R_2$ may be joined to form a saturated cyclic 6-membered piperidine or morpholine ring.

II. SUMMARY OF THE INVENTION

Many of the antimicrobials of the prior art are ineffective against gram negative bacteria, have toxicity, and/or environmental problems. It is an object of this invention to provide antimicrobial compounds which have excellent activity against a broad spectrum of fungi and bacteria, and have favorable toxicological and environmental profiles.

Their objects and others are achieved by the present invention which comprises compounds having antimicrobial activity having the formula:

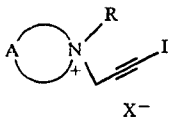

(I)

wherein

R is selected from (A) ($C_1$ to $C_{20}$) straight or branched alkyl, optionally substituted with hydroxy, halogen, alkoxy, phenoxy, or —C(=O)R' wherein R' is selected from ($C_1$–$C_{20}$)alkyl, ($C_1$–$C_{20}$)akloxy, phenoxy, or NHR'' wherein R'' is ($C_1$–$C_6$)alkyl or phenyl; (B) benzyl; (C) phenethyl; (D) cyanoethyl; (E) 2-cyanoethyl; (F) propargyl; and (G) allyl;

X=halogen (chlorine, bromine, or iodine), phosphate, acetate, benzoate, citrate, tartate, alkyl- or arylsulfonate, alkylsulfate; and

represents a 3-to 7-membered ring that contains at least one nitrogen atom optionally substituted with one or more substitutents selected from ($C_1$–$C_3$)alkyl, halo, and carboxyl, said ring optionally containing one or two hetreroatoms in addition to said one nitrogen atom, selected from sulfur, oxygen, and a second nitrogen.

III. DETAILED DESCRIPTION OF THE INVENTION AND THE PREFERRED EMBODIMENTS

Preferred compounds of the invention are those wherein R=$C_{10}$ to $C_{16}$ alkyl,

is pyrrolidinium, piperidinium, morpholinium, dimethylmorpholinium, or tetramethylmorpholinium, and X is bezenesulfonate or methane sulfonate. Preferred compounds include the following:

1. 1-(2-hydroxyethyl)-1-(3-iodopropargyl)-pyrrolidinium 4-methylbenzenesulfonate
2. 1-(12-hydroxydodecyl)-1-(3-iodopropargyl)-pyrrolidinium 4-methylbenzenesulfonate
3. 1-(8-hydroxyoctyl)-1-(3-iodopropargyl)-pyrrolidinium 4-methylbenzenesulfonate
4. 1-(7-hydroxyheptyl)-1-(3-iodopropargyl)-pyrrolidinium 4-methybenzenesulfonate
5. 1-(9-hydroxynonyl)-1-(3-iodopropargyl)-pyrrolidinium 4-methylbenzenesulfonate
6. 1-tetradecyl-1-(3-iodopropargyt)-pyrrolidinium 4-methylbenzenesulfonate
7. 1-hexadecyl-1-(3-iodopropargyl)-pyrrolidinium 4-methylbenzenesulfonate
8. 1-tridecyl-1-(3-iodopropargyl)-pyrrolidinium 4-methylbenzenesulfonate
9. 1-butyl-1-(3-iodopropargyl)-pyrrolidinium 4-methylbenzenesulfonate
10. 1-pentadecyl-1-(3-iodopropargyl)-pyrrolidinium 4-methylbenzenesulfonate
11. 1-decyl-1-(3-iodopropargyl-pyrrolidinium 4-methylbenzenesulfonate
12. 1-octyl-1-(3-iodopropargyl)-pyrrolidinium 4-methylbenzenesulfonate
13. 1-dodecyl-1-(3-iodopropargyl)-pyrrolidinium 4-methylbenzenesulfonate
14. 1-hexyl-1-(3-iodopropargyl)-pyrrolidinium 4-methylbenzenesulfonate
15. 1-undecyl-1-(3-iodopropargyl)-pyrrolidinium 4-methylbenzenesulfonate
16. t-octadecyl-1-(3-iodopropargyl)-pyrrolidinium 4-methylbenzenesulfonate
17. -methyl-1-(3-iodopropargyl)-piperidinium 4-methylbenzenesulfonate
18. 1-(2-hydroxyethyl)-1-(3-iodopropargyl)-piperidinium 4-methylbenzenesulfonate
19. 1-(11-hydroxyundecyl)-1-(3-iodopropargyl)-piperidinium 4-methylbenzenesulfonate
20. 1-(12-hydroxydodecyl)-1-(3-iodopropargyl)-piperidinium 4-methylbenzenesulfonate
21. 1-(9-hydroxynonyl)-1-(3-iodopropargyl)-piperidinium 4-methylbenzenesulfonate
22. 1-(2-ethoxycarbonylethyl)-1-(3-iodopropargyl)-piperidinium 4-methylbenzenesulfonate
23. 1-(8-hydroxyoctyl)-1-(3-iodopropargyl )-1-piperidinium 4-methylbenzenesulfonate
24. 1-(7-hydroxyheptyl)-1-(3-iodopropargyl)-piperidinium- 4methylbenzenesulfonate
25. 1-(tetradecyl)-1-(3-iodopropargyl)-piperidinium 4-methylbenzenesulfonate
26. 1-(hexadecyl)-1-(3-iodopropargyl)-piperidinium 4-methylbenzenesulfonate
27. 1-(12-hydroxydodecyl)-1-(3-iodopropargyl)-hexamethyleneiminium 4-methylbenzenesulfonate
28. 4-tetradecyl-4-(3-iodopropargyl)-morpholinium 4-methylbenzenesulfonate
29. 4-methyl-4-(3-iodopropargl)-morpholinium 4-methylbenzenesulfonate
30. 1-dodecyl-1-(3-iodopropargyl)-pyrrolidinium benzenesulfonate
31. 1-tridecyl-1-(3-iodopropargyl)-pyrrolidinium benzenesulfonate
32. 1-hexadecyl-1-(3-iodopropargy)-pyrrolidinium benzenesulfonate
33. 1-pentadecyl-1-(3-iodopropargyl)-pyrrolidinium benzenesulfonate
34. 1-tetradecyl-1-(3-iodopropargyl)-pyrrolidinium benzenesulfonate
35. 1-hexadecyl-1-(3-iodopropargyl)-pyrrolidinium methanesulfonate
36. 1-tridecyl-1-(3-iodopropargyl)-pyrrolidinium methanesulfonate
37. 1-dodecyl-1-(3-iodopropargyl)-pyrrolidinium methanesulfonate
38. 1-pentadecyl-1-(3-iodopropargyl)-pyrrolidinium methanesulfonate
39. 1-tetradecyl-1-(3-iodopropargyl)-pyrrolidinium methanesulfonate
40. 1-hexadecyl-1-(3-iodopropargyt)-morpholinium methanesulfonate
41. 4-tetradecyl-4-(3-iodoprolyargyl)-morpholinium benzenesulfonate
42. 4-tetradecyl-4-(3-iodopropargyl)-morpholinium methanesulfonate 43. 4-tetradecyl-4-(3-iodopropargyl)-2,6-dimethylmorpholinium 4-methylbenzenesulfonate
44. 1-hexadecyl-1-(3-iodopropargyl)-hexamethyleneiminium 4-methylbenzenesulfonate
45. 1-tetradecyl-1-(3-iodopropargyl)-hexamethyleneiminium 4-methylbenzenesulfonate
46. 4-hexadecyl-4-(3-iodopropargyl)-2,6-dimethylmorpholinium 4-methylbenzenesulfonate
47. 4-hexadecyl-4-(3-iodopropargyl)-2,6-dimethylmorpholinium benzenesulfonate
48. 4-hexadecyl-4-(3-iodopropargyl)-2,6-dimethylmorpholinium methanesulfonate
49. 4-hexadecyl-4-(3-iodopropargyl)-morpholinium 4-methylbenzenesulfonate
50. 4-hexadecyl-4-(3-iodopropargyl)-morpholinium benzenesulfonate
51. 1-(tetradecyl)-1-(3-iodopropargyl)-2-methyl-piperidinium benzenesulfonate
52. 1-(tetradecyl)-1-(3-iodopropargyl)-4-methyl-piperidinium benzenesulfonate
53. 1-(tetradecyl)-1-(3-iodopropargyl)-1,2,3,6-tetrahydropyridinium benzenesulfonate
54. 1-(tetradecyl)-1-(3-iodopropargyl)-2-methyl-piperidinium 4methylbenzenesulfonate
55. 1-(tetradecyl)-1-(3-iodopropargyl)-2-methyl-piperidinium methanesulfonate
56. 1-(tetradecyl)-1-(3-iodopropargyl)-imidazolinium benzenesulfonate
57. 4-(tetradecyl)-4-(3-iodopropargyl)-thiomorpholinium benzenesulfonate
58. 3-(tetradecyt)-3-(3-iodopropargyl)-imidazolidinium benzenesulfonate
59. 1-tetradecyl-1-(3-iodopropargyl)-piperidinium benzenesulfonate
60. 1-hexadecyl-1-(3-iodopropargyl)-piperidinium benzenesulfonate
61. 1-hexadecyl-1-(3-iodopropargyl)-piperidinium methanesulfonate
62. 1-tetradecyl-1-(3-iodopropargyl)-piperidinium methanesulfonate
63. 1-(dodecyloxycarbonyl)methyl-1-(3-iodopropargyl)-pyrrolidinium 4-methylbenzenesulfonate
64. 1-(dodecyloxycarbonyl)methyl-1-(3-iodopropargyl)-pyrrolidinium benzenesulfonate
65. 1-(decyioxycarbonyl)methyl-1-(3-iodopropargyl)-pyrrolidinium 4methylbenzenesulfonate
66. 4-(decyioxycarbonyl)methyl-4-(3-iodopropargyl)-morpholiniurn 4methylbenzenesulfonate
67. 4-(decyloxycarbonyl)methyl-4-(3-iodopropargyl)-morpholinium benzenesulfonate
68. 4-(dodecyloxycarbonyl)methyl-4-(3-iodopropargyl)-morpholinium 4-methylbenzenesulfonate
69. 1-tetradecyl-1-(3-iodopropargyl)-pyrrolidinium bromide
70. 1-(decyloxycarbonyl)methyl-1-(3-iodopropargyt)-pyrrolidinium benzenesulfonate
71. 4-tetradecyl-4-(3-iodopropargyl)-morpholinium bromide
72. 4-tetradecyl-4-(3-iodopropargyl)-rnorpholinium iodide
73. 4-benzyl-4-(3-iodopropargyi )-morpholinium 4-methylbenzenesulfonate
74. 4-benzyl-4-(3-iodopropargyl)-morpholinium methanesulfonate
75. 1-(dodecyloxycarbonyl)methyl-1-(3-iodopropargyl)-pyrrolidinium methanesulfonate
76. 4-(dodecyloxycarbonyl)methyl-4-(3-iodopropargyl)-morpholinium methanesulfonate
77. 1-n-butyl-1-(3-iodopropargyl)-pyrrolidinium bromide
78. 1-decyl-1-(3-iodopropargyl )-pyrrolidinium bromide
79. 1-dodecyl-1-(3-iodopropargyl)-pyrrolidinium bromide
80. 1-hexadecyl-1-(3-iodopropargyl)-pyrrolidinium bromide
81. 4-[5-(hexyloxycarbonyl)]pentyl-4-(3-iodopropargyl)-morpholinium 4-methylbenzenesulfonate
82. 1-[5-(hexyloxycarbonyl)]pentyl-1-(3-iodopropargyl)-pyrrolidinium 4-methylbenzenesulfonate
83. 4-[5-(hexyloxycarbonyl)]pentyl-4-(3-iodopropargyl)-morpholinium methanesulfonate
84. 1-[5-(hexyloxycarbonyl)]pentyl-1-(3-iodopropargyl)-pyrrolidinium methanesulfonate
85. 1-tetradecyl-1-(3-iodoparygyl)-piperidinium n-butylsulfonate
86. 4-tetradecyl-4-(3-iodopropargyl)-morpholinium n-butylsulfonate
87. 1.-tetradecyl-1-(3-iodopropargyl)-pyrrolidinium n-butylsulfonate
88. 4-pentadecyl-4-(3-iodopropargyl)-morpholinium methanesulfonate
89. 4-tridecyl-4-(3-iodopropargyl)-morpholinium methanesulfonate
90. 4-dodecyl-4-(3-iodopropargyl)-morpholinium methanesulfonate
91. 4-decyl-4-(3-iodopropargyl)-morpholinium methanesulfonate
92. 4-n-octyl-4-(3-iodopropargyl)-morpholinium methanesulfonate
93. 4-n-butyl-4-(3-iodopropargyl)-morpholinium methanesulfonate
94. 4-ethyl-4-(3-iodopropargyl)-morpholinium methanesulfonate
95. 4-[2-(decyloxycarbonyl)]ethyl-4-(3-iodopropargyl)-morpholinium methanesulfonate
96. 4-[2-(decyloxycarbonyl)]ethyl-4-)3-iodopropargyl)-morpholinium 4-methanesulfonate
97. 1-[2-(decyloxycarbonyl)]ethyl-1-(3-iodopropargyl)-pyrrolidinium 4-methylbenzenesulfonate
98. 1-[2-(decyloxycarbonyl)]ethyl-1-(3-iodopropargyl)-pyrrolidinium methanesulfonte
99. 4-n-butyl-4-(3-iodopropargyl)-morpholinium bromide
100. 4-hexadecyl-4-(3-iodopropargyl)-morpholinium bromide
101. 4-dodecyl-4-(3-iodopropargyl)-morpholinium bromide Table 1 shows the structures and the physical data of these representative compounds.

Structures and Physical Data

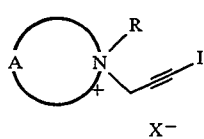

(I)

| No. | (A-N ring) | R | X | Melting Point |
|---|---|---|---|---|
| 1 | pyrrolidine | C₂H₄—OH | OSO₂-C₆H₄-CH₃ | 136–138° C. |
| 2 | pyrrolidine | C₁₂H₂₄—OH | OSO₂-C₆H₄-CH₃ | 65–70° C. |
| 3 | pyrrolidine | C₈H₁₆—OH | OSO₂-C₆H₄-CH₃ | 61–67° C. |
| 4 | pyrrolidine | C₇H₁₄—OH | OSO₂-C₆H₄-CH₃ | oil |
| 5 | pyrrolidine | C₉H₁₈—OH | OSO₂-C₆H₄-CH₃ | 89–92° C. |
| 6 | pyrrolidine | C₁₄H₂₉-n | OSO₂-C₆H₄-CH₃ | 141–143° C. |
| 7 | pyrrolidine | C₁₆H₃₃-n | OSO₂-C₆H₄-CH₃ | 139–144° C. |
| 8 | pyrrolidine | C₁₃H₂₇-n | OSO₂-C₆H₄-CH₃ | 140–142° C. |
| 9 | pyrrolidine | C₄H₉-n | OSO₂-C₆H₄-CH₃ | 140–143° C. |
| 10 | pyrrolidine | C₁₅H₃₁-n | OSO₂-C₆H₄-CH₃ | 143–144° C. |
| 11 | pyrrolidine | C₁₀H₂₁-n | OSO₂-C₆H₄-CH₃ | 137–138° C. |

-continued

Structures and Physical Data $$\text{(I)}$$

A ring with N⁺–R, N⁺–CH₂–C≡C–I, X⁻

| No. | A-N ring | R | X | Melting Point |
|---|---|---|---|---|
| 12 | pyrrolidine | C₈H₁₇-n | OSO₂–C₆H₄–CH₃ | 136–138° C. |
| 13 | pyrrolidine | C₁₂H₂₅-n | OSO₂–C₆H₄–CH₃ | 140–141° C. |
| 14 | pyrrolidine | C₆H₁₃-n | OSO₂–C₆H₄–CH₃ | 122–124° C. |
| 15 | pyrrolidine | C₁H₂₃-n | OSO₂–C₆H₄–CH₃ | 140–141° C. |
| 16 | pyrrolidine | C₈₁H₃₇-n | OSO₂–C₆H₄–CH₃ | 138–141° C. |
| 17 | piperidine | CH₃ | OSO₂–C₆H₄–CH₃ | 174–178° C. |
| 18 | piperidine | C₂H₄–OH | OSO₂–C₆H₄–CH₃ | 109–112° C. |
| 19 | piperidine | C₁₁H₂₂–OH | OSO₂–C₆H₄–CH₃ | 89–93° C. |
| 20 | piperidine | C₁₂H₂₄–OH | OSO₂–C₆H₄–CH₃ | 91–95° C. |
| 21 | piperidine | C₉H₁₈–OH | OSO₂–C₆H₄–CH₃ | 93–98° C. |
| 22 | piperidine | C₂H₄–CO₂Et | OSO₂–C₆H₄–CH₃ | 95–99° C. |

-continued

Structures and Physical Data

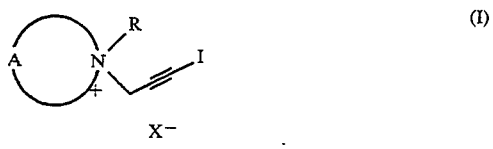

(I)

| No. | A-N ring | R | X | Melting Point |
|---|---|---|---|---|
| 23 | piperidine | $C_8H_{16}$—OH | $OSO_2$-C$_6$H$_4$-CH$_3$ | 129–135° C. |
| 24 | piperidine | $C_7H_{14}$—OH | $OSO_2$-C$_6$H$_4$-CH$_3$ | 100–108° C. |
| 25 | piperidine | $C_{14}H_{29}$-n | $OSO_2$-C$_6$H$_4$-CH$_3$ | 140–144° C. |
| 26 | piperidine | $C_{16}H_{33}$-n | $OSO_2$-C$_6$H$_4$-CH$_3$ | 148–150° C. |
| 27 | azepane | $C_{12}H_{24}$—OH | $OSO_2$-C$_6$H$_4$-CH$_3$ | 75–79° C. |
| 28 | morpholine | $C_{14}H_{29}$-n | $OSO_2$-C$_6$H$_4$-CH$_3$ | 153–154° C. |
| 29 | morpholine | $CH_3$ | $OSO_2$-C$_6$H$_4$-CH$_3$ | 130–137° C. |
| 30 | pyrrolidine | $C_{12}H_{25}$-n | $OSO_2$-C$_6$H$_5$ | 95–97° C. |
| 31 | pyrrolidine | $C_{13}H_{27}$-n | $OSO_2$-C$_6$H$_5$ | 95–100° C. |
| 32 | pyrrolidine | $C_{16}H_{33}$-n | $OSO_2$-C$_6$H$_5$ | 110–111° C. |
| 33 | pyrrolidine | $C_{15}H_{31}$-n | $OSO_2$-C$_6$H$_5$ | 107–109° C. |

-continued

Structures and Physical Data $$\text{(I)}\quad \underset{X^-}{\overset{R}{\underset{|}{A\!\!\frown\!\!N^+\!\!-\!\!CH_2C\!\equiv\!C\!-\!I}}}$$

| No. | A⌒N | R | X | Melting Point |
|---|---|---|---|---|
| 34 | pyrrolidine | $C_{14}H_{29}$-n | $OSO_2$–C$_6$H$_5$ | 104–106° C. |
| 35 | pyrrolidine | $C_{16}H_{33}$-n | $OSO_2 \cdot CH_3$ | 113–117° C. |
| 36 | pyrrolidine | $C_{13}H_{27}$-n | $OSO_2 \cdot CH_3$ | 100–105° C. |
| 37 | pyrrolidine | $C_{12}H_{25}$-n | $OSO_2 \cdot CH_3$ | 108–112° C. |
| 38 | pyrrolidine | $C_{15}H_{31}$-n | $OSO_2 \cdot CH_3$ | 113–118° C. |
| 39 | pyrrolidine | $C_{14}H_{29}$-n | $OSO_2 \cdot CH_3$ | 85–90° C. |
| 40 | morpholine | $C_{16}H_{33}$-n | $OSO_2 \cdot CH_3$ | 111–114° C. |
| 41 | morpholine | $C_{14}H_{29}$-n | $OSO_2$–C$_6$H$_5$ | 134–136° C. |
| 42 | morpholine | $C_{14}H_{29}$-n | $OSO_2 \cdot CH_3$ | 108–112° C. |
| 43 | 2,6-dimethylmorpholine | $C_{14}H_{29}$-n | $OSO_2$–C$_6$H$_4$–CH$_3$ | 105–109° C. |
| 44 | hexamethyleneimine | $C_{16}H_{33}$-n | $OSO_2$–C$_6$H$_4$–CH$_3$ | 80–85° C. |

-continued

Structures and Physical Data $$\text{(I)}\quad \underset{X^-}{\overset{R}{\underset{|}{A-N^+-CH_2-C\equiv C-I}}}$$

[Ring structure: A—N]

| No. | A (ring) | R | X | Melting Point |
|---|---|---|---|---|
| 45 | azepane (7-membered N ring) | $C_{14}H_{29}$-n | $OSO_2$–C$_6$H$_4$–CH$_3$ (p-tolyl) | 60–65° C. |
| 46 | 2,6-dimethylmorpholine | $C_{16}H_{33}$-n | $OSO_2$–C$_6$H$_4$–CH$_3$ | glassy |
| 47 | 2,6-dimethylmorpholine | $C_{16}H_{33}$-n | $OSO_2$–C$_6$H$_5$ | glassy |
| 48 | 2,6-dimethylmorpholine | $C_{16}H_{33}$-n | $OSO_2\cdot CH_3$ | glassy |
| 49 | morpholine | $C_{16}H_{33}$-n | $OSO_2$–C$_6$H$_4$–CH$_3$ | 152–154° C. |
| 50 | morpholine | $C_{16}H_{33}$-n | $OSO_2$–C$_6$H$_5$ | 134–136° C. |
| 51 | 2-methylpiperidine | $C_{14}H_{29}$-n | $OSO_2$–C$_6$H$_5$ | viscous oil |
| 52 | 4-methylpiperidine | $C_{14}H_{29}$-n | $OSO_2$–C$_6$H$_5$ | viscous oil |
| 53 | 1,2,3,6-tetrahydropyridine | $C_{14}H_{29}$-n | $OSO_2$–C$_6$H$_5$ | 90–94° C. |

-continued
Structures and Physical Data $$\underset{X^-}{\overset{R}{\underset{A\diagup N^+\diagdown CH_2-C\equiv C-I}{}}}\quad (I)$$

| No. | A-N ring | R | X | Melting Point |
|---|---|---|---|---|
| 54 | 2-methylpiperidine | $C_{14}H_{29}$-n | $OSO_2$-C$_6$H$_4$-CH$_3$ (p-tolyl) | viscous oil |
| 55 | 2-methylpiperidine | $C_{14}H_{29}$-n | $OSO_2.CH_3$ | viscous oil |
| 56 | imidazole | $C_{14}H_{29}$-n | $OSO_2$-C$_6$H$_5$ | 116–120° C. |
| 57 | thiomorpholine | $C_{14}H_{29}$-n | $OSO_2$-C$_6$H$_5$ | 173–177° C. |
| 58 | thiazolidine | $C_{14}H_{29}$-n | $OSO_2$-C$_6$H$_5$ | viscous oil |
| 59 | piperidine | $C_{14}H_{29}$-n | $OSO_2$-C$_6$H$_5$ | 128–130° C. |
| 60 | piperidine | $C_{16}H_{33}$-n | $OSO_2$-C$_6$H$_5$ | 136–139° C. |
| 61 | piperidine | $C_{16}H_{33}$-n | $OSO_2.CH_3$ | semi-solid |
| 62 | piperidine | $C_{14}H_{29}$-n | $OSO_2.CH_3$ | semi-solid |
| 63 | pyrrolidine | $CH_2COOC_{12}H_{25}$ | $OSO_2$-C$_6$H$_4$-CH$_3$ (p-tolyl) | 104–106° C. |
| 64 | pyrrolidine | $CH_2COOC_{12}H_{25}$ | $OSO_2$-C$_6$H$_5$ | 81–83° C. |

-continued

Structures and Physical Data $$\underset{X^-}{\overset{R}{\underset{|}{A\frown N^+\!\!-\!\!CH_2\!-\!C\!\equiv\!C\!-\!I}}} \quad (I)$$

| No. | A⌒N | R | X | Melting Point |
|---|---|---|---|---|
| 65 | pyrrolidine (N in 5-ring) | $CH_2COOC_{10}H_{21}$ | $OSO_2$-C$_6$H$_4$-$CH_3$ (p-tosylate) | 108–109° C. |
| 66 | morpholine (O,N in 6-ring) | $CH_2COOC_{10}H_{21}$ | $OSO_2$-C$_6$H$_4$-$CH_3$ | semi-solid |
| 67 | morpholine | $CH_2COOC_{10}H_{21}$ | $OSO_2$-C$_6$H$_5$ | semi-solid |
| 68 | morpholine | $CH_2COOC_{12}H_{25}$ | $OSO_2$-C$_6$H$_4$-$CH_3$ | semi-solid |
| 69 | pyrrolidine | $C_{14}H_{29}$-n | Br | semi-solid |
| 70 | pyrrolidine | $CH_2COOC_{10}H_{21}$ | $OSO_2$-C$_6$H$_5$ | 80–82° C. |
| 71 | morpholine | $C_{14}H_{29}$-n | Br | 141–144° C. |
| 72 | morpholine | $C_{14}H_{29}$-n | I | 85–88° C. |
| 73 | morpholine | Benzyl | $OSO_2$-C$_6$H$_4$-$CH_3$ | 161–165° C. |
| 74 | morpholine | Benzyl | $OSO_2.CH_3$ | 168–170° C. |
| 75 | pyrrolidine | $CH_2COOC_{12}H_{25}$ | $OSO_2.CH_3$ | 50–53° C. |

-continued

Structures and Physical Data $$\text{(I)}$$

A ring with N+ bearing R and CH2-C≡C-I, with counterion X−

| No. | A-N ring | R | X | Melting Point |
|---|---|---|---|---|
| 76 | morpholine (O, N) | CH$_2$COOC$_{12}$H$_{25}$ | OSO$_2$.CH$_3$ | semi-solid |
| 77 | pyrrolidine (N) | C$_4$H$_9$-n | Br | 169–172° C. |
| 78 | pyrrolidine (N) | C$_{10}$H$_{21}$-n | Br | 118–121° C. |
| 79 | pyrrolidine (N) | C$_{12}$H$_{25}$-n | Br | semi-solid |
| 80 | pyrrolidine (N) | C$_{16}$H$_{33}$-n | Br | 70–73° C. |
| 81 | morpholine (O, N) | (CH$_2$)$_5$COOC$_6$H$_{13}$ | OSO$_2$-C$_6$H$_4$-CH$_3$ | 124–126° C. |
| 82 | pyrrolidine (N) | (CH$_2$)$_5$COOC$_6$H$_{13}$ | OSO$_2$-C$_6$H$_4$-CH$_3$ | 75–77° C. |
| 83 | morpholine (O, N) | (CH$_2$)$_5$COOC$_6$H$_{13}$ | OSO$_2$.CH$_3$ | semi-solid |
| 84 | pyrrolidine (N) | (CH$_2$)$_5$COOC$_6$H$_{13}$ | OSO$_2$.CH$_3$ | semi-solid |
| 85 | piperidine (N) | C$_{14}$H$_{29}$-n | OSO$_2$C$_4$H$_9$-n | 145–150° C. |
| 86 | morpholine (O, N) | C$_{14}$H$_{29}$-n | OSO$_2$C$_4$H$_9$-n | 140–143° C. |

-continued
Structures and Physical Data

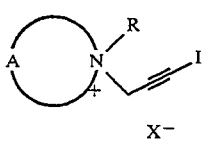  (I)

| No. | 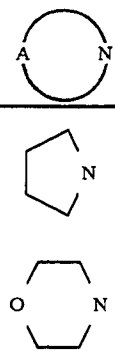 | R | X | Melting Point |
|---|---|---|---|---|
| 87 |  pyrrolidine | $C_{14}H_{29}$-n | $OSO_2C_4H_9$-n | semi-solid |
| 88 | 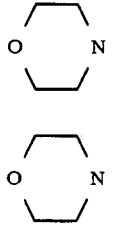 morpholine | $C_{15}H_{31}$-n | $OSO_2.CH_3$ | 111–113° C. |
| 89 | morpholine | $C_{13}H_{27}$-n | $OSO_2.CH_3$ | 110–113° C. |
| 90 | morpholine | $C_{12}H_{25}$-n | $OSO_2.CH_3$ | glassy |
| 91 | morpholine | $C_{10}H_{21}$-n | $OSO_2.CH_3$ | semi-solid |
| 92 | morpholine | $C_8H_{17}$-n | $OSO_2.CH_3$ | semi-solid |
| 93 | morpholine | $C_4H_9$-n | $OSO_2.CH_3$ | 64–65° C. |
| 94 | morpholine | $C_2H_5$ | $OSO_2.CH_3$ | 155–159° C. |
| 95 | morpholine | $(CH_2)_2CO_2C_{10}H_{21}$ | $OSO_2$-C$_6$H$_4$-$CH_3$ | semi-solid |
| 96 | morpholine | $(CH_2)_2CO_2C_{10}H_{21}$ | $OSO_2.CH_3$ | semi-solid |
| 97 | pyrrolidine | $(CH_2)_2CO_2C_{10}H_{21}$ | $OSO_2$-C$_6$H$_4$-$CH_3$ | 75–78° C. |

-continued

Structures and Physical Data

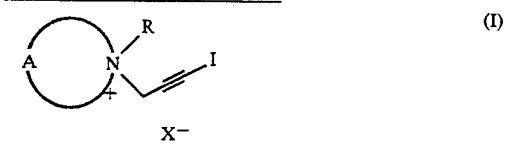

| No. | ⟨A—N⟩ | R | X | Melting Point |
|---|---|---|---|---|
| 98 | (pyrrolidine) | (CH₂)₂CO₂C₁₀H₂₁ | OSO₂.CH₃ | semi-solid |
| 99 | (morpholine) | C₄H₉-n | Br | 190–191° C. |
| 100 | (morpholine) | C₁₆H₃₃-n | Br | semi-solid |
| 101 | (morpholine) | C₁₂H₂₅-n | Br | semi-solid |

Compounds of the invention can be prepared by the following reaction:

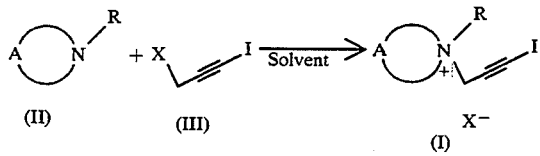

Generally, a tertiary cyclic amine of the formula (II) can be reacted with an iodopropargyl compound of the formula (III), in which X represents halogen or a sulfonate group, in the presence of a suitable solvent at temperature between 0° and 100° C.

The compounds of formula (II) and formula (III) are generally commercially available or can be prepared by known methods in the literature. Examples of compounds of formula (II) are 1-methylpiperidine, 1-butyl-pyrrolidine, 1-(2-hydroxyethyl)-piperidine. Examples of compounds of formula (III) are 3-iodopropargyl-1-chloride, 3-iodopropargyl-1-bromide, and 3-iodopropargyl-1-(4-methylbenzene)sulfonate.

Alternatively, the compounds of the invention can be prepared by the following reaction:

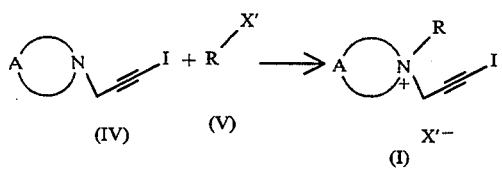

wherein X' is either halogen, alkyl sulfate, alkyl sulfonate, or aryl sulfonate.

The following examples illustrate a few embodiments of the invention.

EXAMPLES

EXAMPLE 1

Preparation of Iodopropargyl Methanesulfonate

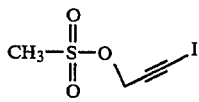

To the solution of 3-iodopropargyl alcohol (5 g, 27.5 mmol) in methylene chloride (150 mL) at 0° C. under nitrogen was added triethylamine (2.8 g, 27.5 mmol). To the above solution, methanesulfonyl chloride (3.2 g, 27.5 mmol) was added dropwise with stirring (magnetic stirrer). The reaction mixture was stirred at 0° to 5° C. for 2 hrs. The reaction mixture was washed with 0.5N HCl (50 mL), diluted sodium bicarbonate (50 mL), water (3×50 mL), and brine. The organic phase was dried over MgSO₄ and filtered. The filtrate was concentrated on a rotary evaporator to afford 5.5 g (yield: 76.9%) of iodopropargyl methanesulfonate as a tan oil. An ¹H NMR spectrum (CDCl₃) showed the desired compound.

EXAMPLE 2

Preparation of Iodopropargyl 4-Methylbenzenesulfonate

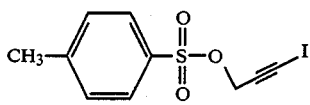

Into a 500 mL 4-neck round bottom flask, equipped with a magnetic stirrer and an addition funnel, in an ice bath were placed iodopropargyl alcohol (10 g, 54.9 mmol) in THF (20 mL) and sodium hydroxide (3.4 g, 84.6 mmol) in water (20 mL) To the above cold mixture was added a solution of p-toluenesulfonyl chloride (10.4 g, 54.95 mmol) in THF (20 mL) from an addition funnel. The reaction mixture was stirred for 2 hrs. below 5° C. The reaction mixture was then poured into ice water and the precipitate was collected by suction-filtration and washed with water. After drying under vacuum, the precipitate afforded 17.2 g (yield: 93.4%) of iodopropargyl 4methylbenzenesulfonate as an off-white solid, mp=75°-78 ° C. An NMR spectrum showed the desired compound.

EXAMPLE 3

Preparation of 1-Tetradecyl-1-(3-Iodopropargyl)-Pyrrolidinium 4-Methylbenzenesulfonate (Compound 6)

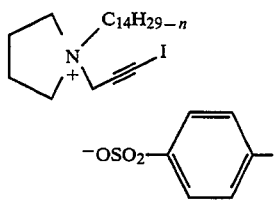

In a 250-mL round bottom flask, equipped with a magnetic stirrer, a heating mantle and reflux condenser, were placed 1-bromotetradecane (10 g, 36 mmol), acetonitrile (100 mL) and pyrrolidine (5.1 g, 72 mmol). The reaction mixture was refluxed for 3 hrs. The reaction mixture was cooled to room temperature and was concentrated on a rotary evaporator to a residue. Water and ethyl acetate were added. The organic phase was separated and washed with saturated sodium chloride solution, dried over anhydrous magnesium sulfate. After filtration, the solvent was evaporated to dryness affording 7.2 g (75% yield) of 1-tetradecylpyrrolidine, as a light yellow semi-solid. This intermediate was subjected to the next step without further purification.

In a 250-mL round bottom flask, equipped with magnetic stirrer, heating mantle, and reflux condenser, were placed 1-tetradecylpyrrolidine (2 g, 7.49 mmol), acetone (20 mL), and iodopropargyl 4-methylbenzenesulfonate (2.6 g, 7.76 mmol). The reaction mixture was stirred at room temperature for 5 hrs. The precipitated product was collected by suction-filtration and washed with ether. After drying under vacuum, a white solid of 1-tetradecyl-1-(3-iodopropargyl)pyrrolidinium 4-methylbenzenesulfonate was obtained, 2.1 g (47% yield). mp=141°-143° C. An NN4R spectrum showed the desired compound. An elemental analysis was also performed:

Elemental Analysis of:

|  | % C | % H | % N | % S | % I |
|---|---|---|---|---|---|
| Calculated | 55.71 | 7.68 | 2.29 | 5.31 | 21.02 |
| Found | 55.89 | 7.93 | 2.32 | 5.25 | 20.73 |

EXAMPLE 4

Preparation of 1-Methyl-1-(3-Iodopropargyl)-Piperidinium 4-Methylbenzenesulfonate (Compound No-17)

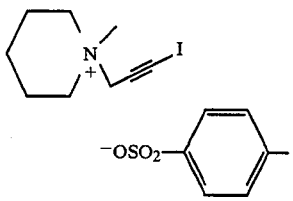

In a 250-mL round bottom flask equipped with a magnetic stirrer were placed 1-methylpiperidine (0.3 g, 3.02 mmol) and ether (10 mL). To the above solution was added iodopropargyl 4-methylbenzenesulfonate (1 g, 2.97 mmol). The mixture was stirred at room temperature for 24 hrs. The white solid was collected by suction-filtration, washed with ether and dried in air affording 0.9 g (68.4% yield), m.p.=174°-178 ° C. An NMR spectrum showed the desired structure and the elemental analysis showed the following:

|  | % C | % H | % I |
|---|---|---|---|
| Calculated | 44.1% | 5.20% | 29.1% |
| Found | 44.2% | 5.13% | 29.0% |

EXAMPLE 5

Preparation of 4-Tetradecyl-4-(3-Iodopropargyl)Morpholidinium 4-Methylbenzenesulfonate (Compound No-28)

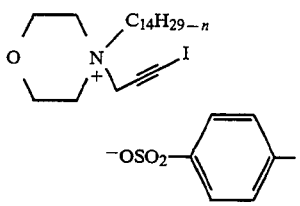

In a 250-mL round bottom flask, equipped with a magnetic stirrer, a heating mantle and reflux condenser, were placed 1-bromotetradecane (15.9 g, 57.3 mmol), acetonitrile (75 mL), and morpholine (10 g, 114.7 mmol). The reaction mixture was refluxed for 4 hrs. The reaction mixture was cooled to room temperature and was concentrated to a residue on a rotary evaporator. Water and ethyl acetate were added. The organic phase was separated and washed with saturated sodium chloride solution, and then dried over anhydrous magnesium sulfate. After filtration, the solvent was evaporated to dryness affording 15.2 g (94% yield) of 4-tetradecylmorpholine as a tan oil. This intermediate was subjected to the next step without further purification.

In a 250-mL round bottom flask, equipped with magnetic stirrer, heating mantle, and reflux condenser, were placed 4-tetradecylmorpholine (1.7 g, 6 mmol), dry acetone (2.5 mL), and iodopropargyl 4methylbenzenesulfonate (2 g, 6 mmol). The reaction mixture was stirred at room temperature for 40 hrs. The solvent was then evaporated to a residue. The residue was made a slurry with ether and the resultant white suspension was suction-filtered, washed with ether and dried under vacuum, affording 2 g (55.5% yield) of 4-tetradecyl-4-(3-iodopropargyl)-morpholidinium 4-methylbenzenesulfonate as a white solid. mp=153°–154 ° C. An NMR spectrum showed the desired compound.

EXAMPLE 6
Biological Activity

Biocidal (bactericidal and fungicidal) evaluations were carried out.

A minimum inhibitory concentration (MIC) value is obtained using a broth, two-fold serial dilution test performed as follows: A stock solution or dispersion of the test compound, typically at a concentration of 1%, is made in a 5:3:2 solvent solution of acetone. methanol, and water. A volume of the stock solution is dispensed into culture media to give an initial starting test concentration of 500 ppm compound.

When the test is ready to be done, each vessel in the dilution series, except the first vessel, contains an equal volume of compound free broth. The first vessel contains twice the volume of broth with the starting concentration of test compound. One half of the broth from the first vessel is transferred to the second vessel- After being mixed, one half the resulting volume is removed from the second vessel and transferred to the third vessel. The entire cycle is repeated sufficiently to give a series of concentrations amounting to 500, 250, 125, 63, 31, 16, 8, and 4, 2, 1, 0.5, 0.25 ppm respectively.

Each vessel is then inoculated with a cell suspension of the appropriate test organism. Bacteria are grown in broth, fungi on agar slants for a time and at a temperature appropriate to the species being tested, and algae are a mixture of green algae and blue-green bacteria grown in a nutrient media. At the end of the growth period, in the case of bacteria, the broth is vortexed to disperse the cells.

In the case of fungi, the spores are harvested by pipetting water onto the slant and dislodging the spores with a sterile loop. The cell/spore suspension is standardized by controlling incubation time, temperature, and the volume of the diluent. The suspension is then used to inoculate the vessels containing the broth compound.

The vessels are then incubated at the appropriate temperature. After the incubation, the vessels are examined for growth/no growth. The minimum inhibitory concentration (MIC) is defined as the lowest concentration of compound that results in complete inhibition of growth of the test organism.

The organisms tested to demonstrate biocidal activity are shorten in the following table:

TABLE 2A

| MICROORGANISMS USED IN THE BIOCIDES TESTS | | | |
|---|---|---|---|
| Name | GRAM | ATCC | Abbreviation used |
| BACTERIA | | | |
| 1. *Pseudomonas aeruginosa* | (−) | 15442 | Psae |
| 2. *Staphylococcus aureus* | (+) | 6538 | Saur |
| 3. *Escherichia coli* | (−) | 11229 | Ecol |
| FUNGUS | | | |
| 4. *Aspergillus niger* | | 6275 | Anig |

The result of minimum inhibitory concentration (MIC) tests of compounds of this invention is shown in Table 2.

TABLE 2

| | Biocidal MIC Results | | | | | | |
|---|---|---|---|---|---|---|---|
| | MIC (ppm) | | | | | | |
| Bacteria: | (G−) Psae | | (G−) Ecol | | (G+) Saur | | (fungus) Anig |
| Media: | M9G | TSB | M9G | TSB | M9G | TSB | TSB |
| Cpd No | | | | | | | |
| 1 | >250 | 125 | — | >250 | 16 | 32 | >250 |
| 2 | >250 | >250 | — | 250 | 32 | 32 | 32 |
| 3 | >500 | >500 | — | >500 | 500 | >500 | >500 |
| 4 | >500 | >500 | >500 | 500 | 500 | 500 | 250 |
| 5 | >500 | >500 | >500 | >500 | 63 | 63 | 250 |
| 6 | 4 | 4 | 4 | 4 | 0.5 | 0.5 | <0.25 |
| 7 | 4 | 8 | 4 | 2 | <0.25 | <0.25 | 1 |
| 8 | 16 | 16 | 2 | 4 | 0.5 | 1 | 1 |
| 9 | 500 | >500 | 500 | 250 | 250 | 250 | 500 |
| 10 | 8 | 250 | 4 | 32 | <0.25 | 1 | <0.25 |
| 11 | 250 | 500 | 16 | 32 | 2 | 16 | 4 |
| 12 | 500 | >500 | 32 | 63 | 2 | 16 | 16 |
| 13 | 32 | 250 | 32 | 32 | 1 | 16 | 16 |
| 14 | 500 | 500 | 250 | 125 | 16 | 16 | 250 |
| 15 | 32 | 32 | 1 | 2 | 0.25 | 0.25 | 16 |
| 16 | 500 | 500 | 16 | 63 | 1 | 1 | 32 |
| 17 | 250 | 125 | — | 250 | 32 | 32 | 125 |
| 18 | 250 | 125 | — | 250 | 16 | 32 | 250 |
| 19 | 250 | 250 | — | 32 | 2 | 16 | 32 |
| 20 | >250 | >250 | — | 250 | 8 | 63 | 125 |
| 21 | >250 | >250 | — | >250 | >250 | >250 | 63 |
| 22 | >250 | >250 | — | >250 | >250 | >250 | 16 |
| 23 | >500 | >500 | — | >500 | 63 | 250 | >500 |
| 24 | >500 | >500 | — | >500 | 63 | 500 | >500 |
| 25 | 8 | 2 | 2 | 16 | 0.25 | 0.25 | 8 |
| 26 | 4 | 16 | 4 | 4 | 0.25 | 0.25 | 16 |
| 27 | >250 | >250 | — | 250 | 16 | 32 | 32 |
| 28 | 4 | 4 | 1 | 2 | 0.25 | 0.25 | 8 |

TABLE 2-continued

Biocidal MIC Results
MIC (ppm)

| Bacteria: | (G−) Psae | | (G−) Ecol | | (G+) Saur | | (fungus) Anig |
|---|---|---|---|---|---|---|---|
| Media: | M9G | TSB | M9G | TSB | M9G | TSB | TSB |
| 29 | 500 | 500 | 250 | 125 | 500 | 500 | 500 |
| 30 | 63 | 63 | 2 | 16 | 1 | 1 | 1 |
| 31 | 32 | 32 | 1 | 16 | 0.5 | <0.25 | 1 |
| 32 | 32 | 125 | 4 | 16 | <0.25 | <0.25 | <0.25 |
| 33 | 8 | 32 | 1 | 2 | <0.25 | <0.25 | <0.25 |
| 34 | 2 | 2 | 0.25 | 0.25 | <0.25 | <0.25 | 0.25 |
| 35 | >500 | >500 | 4 | 63 | 0.5 | 0.25 | 4 |
| 36 | 32 | 63 | 2 | 8 | <0.25 | <0.25 | 1 |
| 37 | 63 | 125 | 2 | 16 | 0.5 | 0.5 | 0.25 |
| 38 | 32 | 63 | 1 | 8 | <0.25 | <0.25 | 0.5 |
| 39 | 63 | 63 | 1 | 2 | <0.25 | <0.25 | 0.5 |
| 40 | 4 | 4 | 0.5 | <0.25 | <0.25 | 0.5 | <0.25 |
| 41 | 2 | 4 | <0.25 | <0.25 | <0.25 | 0.5 | 2 |
| 42 | 1 | 4 | <0.25 | <0.25 | <0.25 | 0.5 | 1 |
| 43 | 2 | 4 | <0.25 | 0.5 | <0.25 | 0.5 | 1 |
| 44 | 8 | 8 | 8 | 16 | 8 | 4 | 8 |
| 45 | 4 | 4 | <0.25 | <0.25 | <0.25 | <0.25 | 1 |
| 46 | 16 | 16 | 8 | 8 | <0.25 | <0.25 | 2 |
| 47 | 8 | 8 | 2 | 2 | <0.25 | <0.25 | 0.5 |
| 48 | 8 | 8 | 2 |  | <0.25 | 0.5 | 1 |
| 49 | 8 | 8 | 1 | 2 | <0.25 | 0.5 | 1 |
| 50 | 8 | 8 | 1 | 1 | <0.25 | 0.5 | 0.5 |
| 51 | 16 | 16 | 4 | 2 | <0.25 | <0.25 | 0.5 |
| 52 | 16 | 16 | 8 | 2 | <0.25 | <0.25 | <0.25 |
| 53 | 8 | 16 | 2 | 1 | <0.25 | <0.25 | <0.25 |
| 54 | 250 | 125 | 8 | 16 | 1 | 8 | 1 |
| 55 | 125 | 125 | 4 | 16 | 1 | 8 | 1 |
| 56 | 8 | 63 | <0.25 | <0.25 | <0.25 | <0.25 | <0.25 |
| 57 | 0.5 | 4 | <0.25 | 0.5 | <0.25 | <0.25 | 0.5 |
| 58 | 125 | >500 | 4 | 8 | 0.5 | 4 | 8 |
| 59 | 32 | 125 | 8 | 16 | 4 | 4 | 8 |
| 60 | 63 | 250 | 2 | 16 | 1 | 2 | 16 |
| 61 | 16 | 125 | 8 | 8 | 2 | 2 | 8 |
| 62 | 16 | 63 | 2 | 4 | 0.25 | 0.25 | 0.25 |
| 63 | 64 | 125 | 2 | 4 | 2 | 4 | 2 |
| 64 | 32 | 32 | 1 | 4 | 0.25 | 0.25 | 8 |
| 65 | 64 | 125 | 2 | 4 | 2 | 1 | 16 |
| 66 | 64 | 250 | 2 | 8 | 0.5 | 8 | 125 |
| 67 | 125 | 250 | 2 | 8 | 0.5 | 8 | 125 |
| 68 | 32 | 64 | 2 | 8 | 0.5 | 2 | 16 |
| 69 | 8 | 32 | 1 | 4 | 0.25 | 0.25 | 4 |
| 70 | 125 | 250 | 2 | 8 | 1 | 2 | 32 |
| 71 | 8 | 32 | 1 | 4 | 0.25 | 0.25 | 4 |
| 72 | 16 | 64 | 0.5 | 4 | 0.25 | 0.25 | 4 |
| 73 | >500 | >500 | 125 | 125 | 125 | 250 | 125 |
| 74 | >500 | >500 | 64 | 125 | 125 | 250 | 64 |
| 75 | 32 | 125 | 2 | 8 | 0.25 | 2 | 8 |
| 76 | 64 | 125 | 2 | 8 | 0.25 | 2 | 32 |
| 77 | >500 | >500 | 64 | 64 | 250 | 250 | >500 |
| 78 | 250 | 500 | 2 | 4 | 0.25 | 2 | 8 |
| 79 | 32 | 64 | 1 | 4 | 0.25 | 1 | 2 |
| 80 | 16 | 125 | 2 | 8 | 0.5 | 0.5 | 1 |
| 81 | >500 | >500 | 64 | 64 | 4 | 16 | 125 |
| 82 | >500 | >500 | 32 | 64 | 2 | 8 | 125 |
| 83 | >500 | >500 | 16 | 32 | 4 | 8 | 125 |
| 84 | >500 | >500 | 16 | 32 | 2 | 8 | 32 |
| 85 | 8 | 32 | 1 | 4 | 0.25 | 0.25 | 4 |
| 86 | 8 | 32 | 2 | 8 | 0.5 | 1 | 8 |
| 87 | 16 | 64 | 2 | 4 | 0.25 | 0.25 | 4 |
| 88 | 8 | 32 | 2 | 4 | 0.25 | 0.25 | 4 |
| 89 | 16 | 64 | 2 | 8 | 1 | 2 | 8 |
| 90 | 16 | 125 | 2 | 4 | 2 | 4 | 16 |
| 91 | 250 | >500 | 4 | 8 | 1 | 8 | 32 |
| 92 | >500 | >500 | 32 | 64 | 8 | 16 | 125 |
| 93 | >500 | >500 | 125 | 125 | >500 | >500 | 500 |
| 94 | >500 | >500 | 125 | 125 | 500 | >500 | >500 |
| 95 | 500 | 500 | 16 | 64 | 32 | 64 | 32 |
| 96 | 500 | >500 | 8 | 64 | 32 | 64 | 16 |
| 97 | 250 | 500 | 16 | 32 | 8 | 16 | 16 |
| 98 | 500 | 500 | 16 | 32 | 8 | 32 | 16 |

From Table 2, the most active compounds are those with R=$C_{10}$ to $C_{16}$. Furthermore, the cyclic quaternary ammonium compounds which contain an iodopropargyl group, such as those in this invention, are surprising in that they have excellent activity against Gram negative bacteria, such as *Pseudomonas aeruginosa* or *Escherichia coli*, when compared with the corresponding cyclic quaternary, ammonium compounds which do not contain an iodopropargyl group.

EXAMPLE 7

Comparative

Table 3 shows the comparison from MIC test results of several representative iodopropargylated cyclic quaternary ammonium compounds of the invention and their corresponding non-iodopropargylated analogues (compound number followed by "A").

The last compound is also a comparative compound and is the tropiumbenzyl sulfonate quat from U.S. Pat. No. 4,521,412, identified as "Bayer analogue."

TABLE 3

Comparison of Iodopropargylated- and Non-iodopropargylate-Quats

| Bacteria: | (G−) Psae | | (G−) Ecol | | (G+) Saur | | (fungus) Anig |
|---|---|---|---|---|---|---|---|
| Media: | M9G | TSB | M9G | TSB | M9G | TSB | TSB |
| Cpd No | | | | | | | |
| 6 | 4 | 4 | 4 | 4 | 0.5 | 0.5 | <0.25 |
| 6A | 125 | 250 | 125 | 250 | <0.25 | <0.25 | <0.25 |
| 34 | 2 | 2 | 0.25 | 0.25 | <0.25 | <0.25 | 0.25 |
| 34A | 125 | 250 | 16 | 32 | 1 | 0.25 | 16 |
| 17 | 250 | 125 | — | 250 | 32 | 32 | 125 |
| 17A | >500 | >500 | >500 | >500 | >500 | >500 | >500 |
| Bayer Analogue | 63 | 125 | 15 | 63 | 32 | 125 | — |

EXAMPLE 8

Comparative

Table 4 shows the comparison of MIC test results of three compounds of the present invention, 1-(tetradecyl)-1-(3-iodopropargyl)-piperidinium 4-methylbenzenesulfonate, 4-tetradecyl-4-(3-iodopropargyl)-morpholinium benzenesulfonate, and 4-tetradecyl-4-(3-iodopropargyl)-morpholinium methanesulfonate (Compounds 25, 41 and 42, respectively) with the two most c;osely related compounds from Japanese Patent 67-026603B, N-(3-iodo-2-propynyl)-piperidine and N-(3-iodo-2-propynyl)-morpholine (Compounds J1 and J2 respectively). These Japanese compounds are the iodopropargyl amines corresponding to the quaternary ammonium compounds of the present invention.

These five compounds were tested side-by-side against six organisms, Pseudomonas aeruginosa (P. aeruginosa), Klebsiella pneumoniae (K. pneumoniae), Enterobacter aerogenes (E. aerogenes), Proteus mirabilis (P. mirabilis), Staphylococcus aureus (S. aureus), and Aspergillus niger (A. niger). The MIC tests were performed as in example 6.

TABLE 4

| | MIC Values (ppm) | | | | |
|---|---|---|---|---|---|
| | Invention Compounds | | | Japanese Compounds | |
| Organism | #25 | #41 | #42 | J1 | J2 |
| P. aeruginosa | 8 | 8 | 16 | >500 | >500 |
| K. Pneumoniae | 4 | 4 | 4 | 125 | 500 |
| E. Aerogenes | 1 | 2 | 1 | 32 | 250 |
| P. mirabilis | 4 | 4 | 4 | 125 | 500 |
| S. aureu | 0.5 | 0.5 | 1 | 125 | 250 |
| A. niger | 8 | 8 | 8 | 16 | 8 |

As can be seen from the data, the quaternary ammonium compounds of the present invention are surprisingly and significantly more active against the organisms tested than those of the Japanese reference.

The compounds of the invention can be used to inhibit the growth of microbes by introducing a microbicidally effective amount of one or more of said compounds onto, into, or at a locus subject to microbial attack. Loci such as wood, paint, adhesive, glue, paper, pulp/paper slurries, textile, leather, plastics, cardboard, lubricants, cosmetics, food, caulking, feed, and industrial cooling water can be protected.

The amount of compound suitable is about 5 to about 300 ppm based on weight of said locus. Generally, the microbicide is applied in a carrier such as water, solvent, or the like.

While the invention has been described in detail, various modifications and alterations should become readily apparent to those skilled in the art without departing from the spirit and scope of the invention.

I claim:

1. Compounds having antimicrobial activity having the formula:

wherein

R is ($C_1$ to $C_5$) alkyl substituted with —C(=O)R' wherein R' is ($C_6$–$C_{12}$) alkoxy;

X=chlorine bromine, iodine, phosphate, acetate, benzoate, citrate, tartrate, alkyl- or aryl-sulfonate, or alkylsulfate; and

represents a 5- to 7-membered ring selected from the group consisting of pyrrolidinium, piperidinium, morpholinium, hexamethyleneiminium, tetrahydropyridinium, immidazolinium, thiormorpholinium, and thiazonlidinium, optionally substituted with one or more ($C_1$–$C_3$)alkyl groups.

2. Compound according to claim 1 selected from the group consisting of 1-(dodecyloxycarbonyl)methyl-1-(3-iodopropargyl)-pyrrolidinium 4-methylbenzenesulfonate 1-(dodecyloxycarbonyl)methyl-1-(3-iodopropargyl)-pyrrolidinium benzenesulfonate 1-(decyioxycarbonyl)methyl-1-(3-iodopropargyl)-pyrrolidinium 4-methylbenzenesulfonate 4-(decyioxycarbonyl)methyl-4-(3-iodopropargyl)-morpholiniurn 4-methylbenzenesulfonate 4-(decyloxycarbonyl)methyl-4-(3-iodopropargyl)-morpholinium benzenesulfonate 4-(dodecyloxycarbonyl)methyl-4-(3-iodopropargyl)-morpholinium 4-methylbenzenesulfonate 1(decyloxycarbonyl)methyl-1-(3-iodopropargyl)-pyrrolidinium benzenesulfonate 1-(dodecyloxycarbonyl)methyl-1-(3iodopropargyl)-pyrrolidinium methanesulfonate 4-(dodecyloxycarbonyl)methyl-4-(3-iodopropargyl)-morpholinium methanesulfonate 4-[5-(hexyloxycarbonyl)]pentyl-4-(3-iodopropargyl)-morpholinium 4-methylbenzenesulfonate 1-[5-(hexyloxycarbonyl)]pentyl-1-(3-iodopropargyl)-pyrrolidinium 4-methylbenzenesulfonate 4-[5-(hexyloxycarbonyl)]pentyl-4-(3-iodopropargyl)-morpholinium methanesulfonate 4-[2-decyloxycarbonyl)]ethyl-4-(3-iodopropargyl-morpholinium 4-methylbenzenesulfonate 4-[2-(decyloxycarbonyl)]ethyl-1-(3-iodopropargyl)-morpholinium-4-methanesulfonate 1-[2-(decyloxycarbonyl]ethyl-1-(3-iodopropargyl)-pyrrolidinium 4-methylbenzenesulfonate 1-[2-(decyloxycarbonyl)]ethyl-1-(3-iodopropargyl)-pyrrolidinium methanesulfonate.

* * * * *